(12) United States Patent
Blair et al.

(10) Patent No.: US 8,551,435 B2
(45) Date of Patent: Oct. 8, 2013

(54) PROCESS FOR REDUCING CONTAMINANTS IN AN INDUSTRIAL FLUID STREAM

(75) Inventors: Alan M. Blair, Southampton (GB); Keith N. Garside, Hampshire (GB); William J. Andrews, Montgomery, IL (US); Kailas B. Sawant, Naperville, IL (US)

(73) Assignee: Nalco Company, Naperville, IL (US)

( * ) Notice: Subject to any disclaimer, the term of this patent is extended or adjusted under 35 U.S.C. 154(b) by 0 days.

(21) Appl. No.: 13/397,131

(22) Filed: Feb. 15, 2012

(65) Prior Publication Data

US 2012/0145001 A1 Jun. 14, 2012

Related U.S. Application Data

(62) Division of application No. 12/494,521, filed on Jun. 30, 2009, now Pat. No. 8,461,335.

(51) Int. Cl.
| | |
|---|---|
| *B01D 53/40* | (2006.01) |
| *B01D 53/48* | (2006.01) |
| *B01D 53/50* | (2006.01) |
| *B01D 53/52* | (2006.01) |
| *B01D 53/96* | (2006.01) |
| *C07D 241/04* | (2006.01) |

(52) U.S. Cl.
USPC ............ 423/228; 423/242.2; 423/242.7; 423/243.01; 423/243.11; 423/437.1; 423/443; 95/156; 95/235; 95/236; 544/402

(58) Field of Classification Search
USPC .......... 544/358, 402; 423/210, 220, 226, 228, 423/140 R, 241, 242.1, 242.2, 242.7, 423/243.01, 243.11, 351, 385, 400, 405, 423/437.1, 443, 240 R; 95/149, 156, 230, 95/232, 233, 235, 236; 548/300.1
See application file for complete search history.

(56) References Cited

U.S. PATENT DOCUMENTS

| 4,094,957 A | 6/1978 | Sartori et al. |
| 4,096,085 A | 6/1978 | Holoman, Jr. et al. |

(Continued)

FOREIGN PATENT DOCUMENTS

| CA | 2651888 | 11/2007 |
| GB | 973903 | * 11/1964 |

(Continued)

OTHER PUBLICATIONS

LookChem.com, "1-Piperazinepropanamine." 2008 (no month). Viewed on Apr. 13, 2012 at http://www.lookchem.com/cas-348/34885-02-4.html.*

(Continued)

*Primary Examiner* — Stuart Hendrickson
*Assistant Examiner* — Daniel Berns
(74) *Attorney, Agent, or Firm* — Edward O. Yonter

(57) ABSTRACT

This invention provides novel processes utilizing compositions comprising substituted polyamines as acid gas scrubbing solutions and methods of using the compositions in an industrial system. The invention relates to the use of such polyamine compounds in industrial processes to remove acidic contaminants from natural and industrial fluid streams, such as natural gas, combustion gas, natural gas, synthesis gas, biogas, and other industrial fluid streams. The compositions and methods of the invention are useful for removal, absorption, or sequestration of acidic contaminants and sulfide contaminants including $CO_2$, $H_2S$, RSH, $CS_2$, COS, and $SO_2$.

20 Claims, 2 Drawing Sheets

(56) References Cited

U.S. PATENT DOCUMENTS

| | | |
|---|---|---|
| 4,217,237 A | 8/1980 | Sartori et al. |
| 4,405,578 A | 9/1983 | Sartori et al. |
| 4,405,583 A | 9/1983 | Stogryn et al. |
| 4,452,763 A | 6/1984 | van de Kraats et al. |
| 4,556,546 A | 12/1985 | Burgoyne, Jr. et al. |
| 5,209,914 A | 5/1993 | Peytavy et al. |
| 5,304,361 A | 4/1994 | Parisi |
| 5,366,709 A | 11/1994 | Peytavy et al. |
| 6,267,939 B1 | 7/2001 | Gemes et al. |
| 6,497,852 B2 | 12/2002 | Chakravarti et al. |
| 6,656,977 B2 | 12/2003 | Slone et al. |
| 6,740,230 B1 | 5/2004 | Hugo et al. |
| 7,481,988 B2 | 1/2009 | Katz et al. |
| 2006/0104877 A1* | 5/2006 | Cadours et al. ............... 423/226 |
| 2008/0025893 A1 | 1/2008 | Asprion et al. |
| 2008/0125314 A1 | 5/2008 | Shim et al. |
| 2008/0236390 A1 | 10/2008 | Anders et al. |

FOREIGN PATENT DOCUMENTS

| | | |
|---|---|---|
| JP | 2006-240966 | 9/2006 |
| WO | 9001804 | 2/1990 |
| WO | 03013699 | 2/2003 |
| WO | 2007077323 | 7/2007 |

OTHER PUBLICATIONS

National Oceanic and Atmospheric Administration (NOAA), "N-aminoethyl piperazine." Jun. 1999. Viewed on Apr. 13, 2012 at http://cameochemicals.noaa.gov/chris/AEP.pdf.*

"1,3-Propanediamine,N1-[3-(dimethylamino)propyl]-N1,N3,N3-trimethyl-.", LookChem.com, 2008, http://www.lookchem.com/chemical-dictionary/en/product_1/3855-32-1/.

"N,N-Bis[3-(dimethylamino)propyl]-N',N'-dimethylpropane-1,3-diamine." LookChem.com, 2008, http://www.lookchem.com/cas-333/33329-35-0.html.

"1,2-Ethanediamine,N1, N1-bis[2-(dimethylamino)ethyl]-N2,N2-dimethyl-.", LookChem.com, 2008, http://www.lookchem.com/cas-335/33527-91-2.html.

Xia et al., "Controlled/"Living" Radical Polymerization. Atom Transfer Radical Polymerization of Acrylates at Ambient Temperature.", Macromolecules, vol. 31, Aug. 5, 1998, pp. 5958-5959.

* cited by examiner

PROCESS FOR REDUCING CONTAMINANTS IN AN INDUSTRIAL FLUID STREAM

CROSS REFERENCE TO RELATED APPLICATIONS

This application is a divisional application of U.S. patent application Ser. No. 12/494,521, filed on Jun. 30, 2009 now U.S. Pat. No. 8,461,335, "Acid Gas Scrubbing Composition," now pending, which is herein incorporated by reference in its entirety.

TECHNICAL FIELD

This invention relates generally to the use of novel compounds as acid gas scrubbing solutions. More specifically, the invention relates to the use of substituted heterocyclic amines and polyamine compounds in industrial processes to remove acidic contaminants from natural and industrial fluid streams, such as natural gas, combustion gas, synthetic gas streams, and hydrocarbon fluids. The invention has particular relevance to processes for removal of carbon dioxide from gas streams having sour gas impurities.

BACKGROUND

Natural gas is a mixture of gaseous hydrocarbons and non-hydrocarbon impurities and contaminants. Removal of, for example, carbon dioxide and acidic sulfide contaminants (e.g., $CO_2$, $H_2S$, RSH, $CS_2$, COS, $SO_2$, etc.) to meet quality and regulatory requirements in natural gas that is fed into distribution pipelines is a major industrial burden. Such contaminants are often corrosive and may also impair the caloric value of the gas. In addition, increasing concerns of global warming from $CO_2$ and other emissions has prompted significant investments into methods of capturing such contaminants more efficiently and economically.

Aqueous solutions of commonly available commodity alkanolamines are generally used as scrubbing solutions (chemical absorbents) in gas processing. The purpose of these scrubbing systems is to remove acidic contaminants from the raw gas stream. As energy sources are being depleted and environmental restrictions are tightening, the economic use of the "bottom of the barrel" in gasification processes is increasing. There are many new projects being sanctioned, most of which would need acid gas clean-up to remove contaminants during processing. Removing $CO_2$ from flue gases is also important for a variety of reasons, such as a secondary $CO_2$ market, enhanced oil recovery, and greenhouse gas reduction.

Weak organic bases, such as monoethanolamine (MEA), diethanolamine (DEA), and methyldiethanolamine (MDEA) comprise many of the typical alkanolamine solvents known in the art. MDEA is known to have advantages for $CO_2$ removal and other acid gas contaminants in high-pressure gas streams. The amount of energy required to regenerate the MDEA is low because it is a relatively weak base and therefore the chemical bond formed during the reaction with $CO_2$ is weaker than with other commonly used alkanolamines. A secondary benefit lies in the nature of the chemical bond formed during absorption. As a tertiary alkanolamine, MDEA reacts with $CO_2$ to form a bicarbonate ion rather than a carbamate, which results in a reaction ratio MDEA to $CO_2$ of 1:1. In contrast, other commonly used primary and secondary alkanolamines preferentially form a carbamate and require a reaction ratio of 2:1. The reaction between $CO_2$ and tertiary alkanolamines (e.g., MDEA) is typically of a greater efficiency than between $CO_2$ and other commonly used primary and secondary alkanolamines. These combined benefits result in a process of greater efficiency and capacity than is possible with commercial primary and secondary alkanolamines such as MEA and DEA.

A disadvantage of using tertiary alkanolamines is that $CO_2$ is indirectly absorbed, resulting in a weak driving force and slow rate of reaction compared to other commercial alkanolamines. In high-pressure gas contacting systems the effect of the weak driving force is minimized due to the higher fraction of $CO_2$ that can be achieved in the liquid resulting from the high $CO_2$ partial pressure in the gas above it. When gasses are contacted at low pressure, the driving force is weak as the partial pressure of $CO_2$ is also weak. Thus, there is no beneficial effect of pressure, and the $CO_2$ equilibrium established between the gas and liquid is low. Tertiary alkanolamines are not normally used in low-pressure applications because of their low equilibrium loading. Other more commonly used primary and secondary amines such as MEA and DEA, which are stronger bases, are used in these applications due to their higher driving force and increased rate of reaction with $CO_2$. In these low-pressure situations, the disadvantage of the inefficient carbamate reaction is outweighed by the greater equilibrium liquid distribution achieved.

In an effort to increase the capacity of MDEA for $CO_2$ at low partial pressure, a number of improvements to the basic MDEA process have been developed. These improvements typically involve the addition of small amounts of primary or secondary amines to the MDEA solution (as described in U.S. Pat. Nos. 5,209,914 and 5,366,709 and PCT Application No. WO 03/1013699). The resulting mixtures are commonly described as formulated or blended MDEA with additives referred to as "catalysts," "absorption accelerators," or "activators" (e.g., U.S. Pat. No. 6,740,230). These additives generally function by increasing the rate of $CO_2$ absorption into the MDEA blend solution at low $CO_2$ partial pressure thereby increasing the fraction of $CO_2$ in the liquid as compared to the MDEA solution alone.

Although effective in the removal of $CO_2$ as described, the commercial application of known formulated solvents has less than ideal operating characteristics. Some of the additives used for formulating have limited solubility in MDEA, which reduces their effectiveness, and their commonly lower boiling (some are not lower) points in turn create difficulties in maintaining their concentration. Moreover, the reaction products of the additives with $CO_2$ are also problematic. As they are stronger organic bases than MDEA these blends have a tendency to require more energy for regeneration and their products have limited solubility. Such characteristics limit their effectiveness and the efficiency of the overall process if their concentration exceeds approximately 20% of the total amine in solution.

There thus exists an industrial need for improved compositions and methods for recovering acidic contaminants from both high and low pressure systems. A particular need exists for products having the benefits of both low-pressure equilibrium capacity of primary or secondary amines and the efficiency of tertiary amines within a single compound of reduced volatility.

SUMMARY

This invention accordingly provides novel compositions for removing carbon dioxide and acidic sulfide contaminants from fluid streams, for example, natural gas, synthesis gas, combustion gas, biogas, and other industrial fluid streams. Through this disclosure reference to gas or fluid streams is intended to encompass, without limitation, all such fluids. In a preferred embodiment, the compositions of the invention are used for removal, absorption, or sequestration of $CO_2$. In other preferred embodiments, the compositions are used for removal of other acidic contaminants, including, without limitation, acidic and sulfide contaminants, such as $CO_2$, $H_2S$, RSH, $CS_2$, COS, and $SO_2$.

In an aspect, the invention is an absorbent liquid composition for absorbing acidic contaminants from fluid streams in an industrial process. The composition includes at least one absorbent component having the following general formula (1).

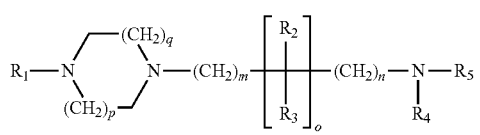

$R_1$ is H, alkyl, aminoalkyl, or structure (2). Preferably, if $R_1$ is H, then at least one of $R_2$, $R_3$, $R_4$, or $R_5$ is not H, and if $R_1$ is structure (2), then at least one of $R_2$, $R_3$, $R_4$, $R_5$, $R_6$, $R_7$, $R_8$, or $R_9$ is not H. $R_2$, $R_3$, $R_4$, $R_5$, $R_6$, $R_7$, $R_8$, and $R_9$ are independently H, alkyl, or aminoalkyl, and each m, n, and o are independently 0, 1, or 2 and p and q are independently 0, 1, 2, 3, or 4.

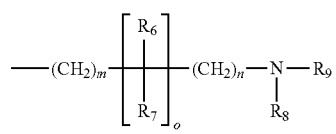

In another aspect, the invention is an absorbent liquid composition for absorbing acidic contaminants from fluid streams in an industrial process. The composition includes at least one absorbent component having the following general formula (3).

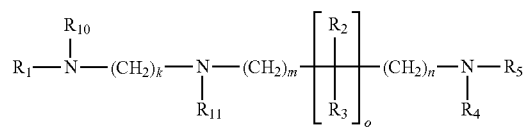

$R_1$ is H, alkyl, or structure (2). Preferably, if $R_1$ is H, then at least one of $R_2$, $R_3$, $R_4$, $R_5$, $R_{10}$, or $R_{11}$ is not H, and if $R_1$ is structure (2), then at least one of $R_2$, $R_3$, $R_4$, $R_5$, $R_6$, $R_7$, $R_8$, $R_9$, $R_{10}$, or $R_{11}$ is not H. $R_2$, $R_3$, $R_4$, $R_5$, $R_6$, $R_7$, $R_8$, $R_9$, $R_{10}$, and $R_{11}$ are independently H, alkyl, or aminoalkyl; each m, n, and o are independently 0, 1, or 2; and k is an integer from 2 to 6.

In another aspect, the invention is a process for reducing acidic contaminants in an industrial fluid stream. The process includes contacting the fluid stream with the described composition to form a washed fluid stream and a rich acid gas scrubbing liquid. At least a portion of the composition including at least a portion of the described absorbent component(s) is regenerated from the rich acid gas scrubbing liquid.

It is an advantage of the invention to provide a novel composition having a specific molecular structure that offers reduced volatility and a working capacity for acidic contaminants greater than commonly used alkanolamine solvents in both low and high-pressure environments.

It is another advantage of the invention to provide a novel composition that reduces acidic contaminants in natural, synthesis, and flue gases and has an increased liquid capacity for acidic contaminants at low gas pressure.

An additional advantage of the invention is to provide a novel composition that reduces acidic contaminants in natural, synthesis, and flue gases and has reduced energy of regeneration.

Another advantage of the invention is to provide a novel composition that reduces acidic contaminants in natural, synthesis, and flue gases and has increased depth of removal.

It is a further advantage of the invention to provide a novel composition that reduces acidic contaminants in natural, synthesis, and flue gases and has improved stability in the process compared to current solvents.

It is yet another advantage of the invention to provide a novel composition that reduces acidic contaminants in natural, synthesis, and flue gases and has a higher boiling point resulting in minimized losses from the process and reduced corrosivity.

Additional features and advantages are described herein, and will be apparent from, the following Detailed Description, Examples, and Figures.

DETAILED DESCRIPTION

The following definitions are intended to be clarifying and are not intended to be limiting.

"Alkyl" refers to a monovalent group derived from a straight or branched chain saturated hydrocarbon by the removal of a single hydrogen atom. Representative alkyl groups include methyl; ethyl; n- and iso-propyl; n-, sec-, iso-, and tert-butyl; $C_5$ to $C_{12}$ groups; eicosanyl ($C_{20}$); heneicosanyl ($C_{21}$); docosyl (behenyl, $C_{22}$); tricosanyl ($C_{23}$); tetracosanyl ($C_{24}$); pentacosyl ($C_{25}$), 3-, 7-, and 13-methylhexadecanyl; and the like. Preferred alkyls include methyl, ethyl, propyl, isopropyl, butyl, and isobutyl.

"Aliphatic amine" and/or "aminoalkyl" refers to an alkyl group having one or more amino substitutions or an amino group having multiple alkyl substitutions. Representative aminoalkyls include aminomethyl, dimethylaminomethyl, diethylaminomethyl, 2-aminoethyl, 2-dimethylaminoethyl, 2-ethylaminoethyl, and the like.

"Amino" or "amine" refers to a group having the structure —NR'R", wherein R' and R" are independently selected from H and alkyl, as previously defined. Additionally, R' and R" taken together may optionally be —$(CH_2)_k$— where k is an integer of from 2 to 6. Representative amino groups include, amino (—$NH_2$), methylamino, ethylamino, n- and iso-propylamino, dimethylamino, methylethylamino, piperidino, and the like.

"Depth of removal" refers to the amount of $CO_2$ that escapes the absorbent solution during peak performance (i.e., $CO_2$ slip), and is an approximation of the efficiency of $CO_2$ absorption.

"Heterocyclic amine" refers to a substituted carbocyclic structure containing at least one nitrogen member in the ring.

"Working capacity" refers to the difference between rich loading and lean loading.

This invention has application in a wide array of industrial processes including gas fields (e.g., marginal, stranded, and sour gas fields), liquefied natural gas (LNG) liquefaction developments, gas-to-liquids (GTL) developments, synthesis gas, and for the removal of $CO_2$ from combustion gases. The disclosed composition may be used in any industrial process, such as single or multi-injection, known in the art or in any specialized high-pressure processes, such as those described in U.S. Pat. No. 6,497,852, "Carbon Dioxide Recovery at High Pressure" and U.S. Pat. No. 7,481,988, "Method for Obtaining a High Pressure Acid Gas Stream by Removal of the Acid Gases from a Fluid Stream," and in PCT patent application no. WO2007077323A1, "Method for Deacidifying a Gas with a Fractionally-Regenerated Absorbent Solution with Control of the Water Content of the Solution."

Figure 1:
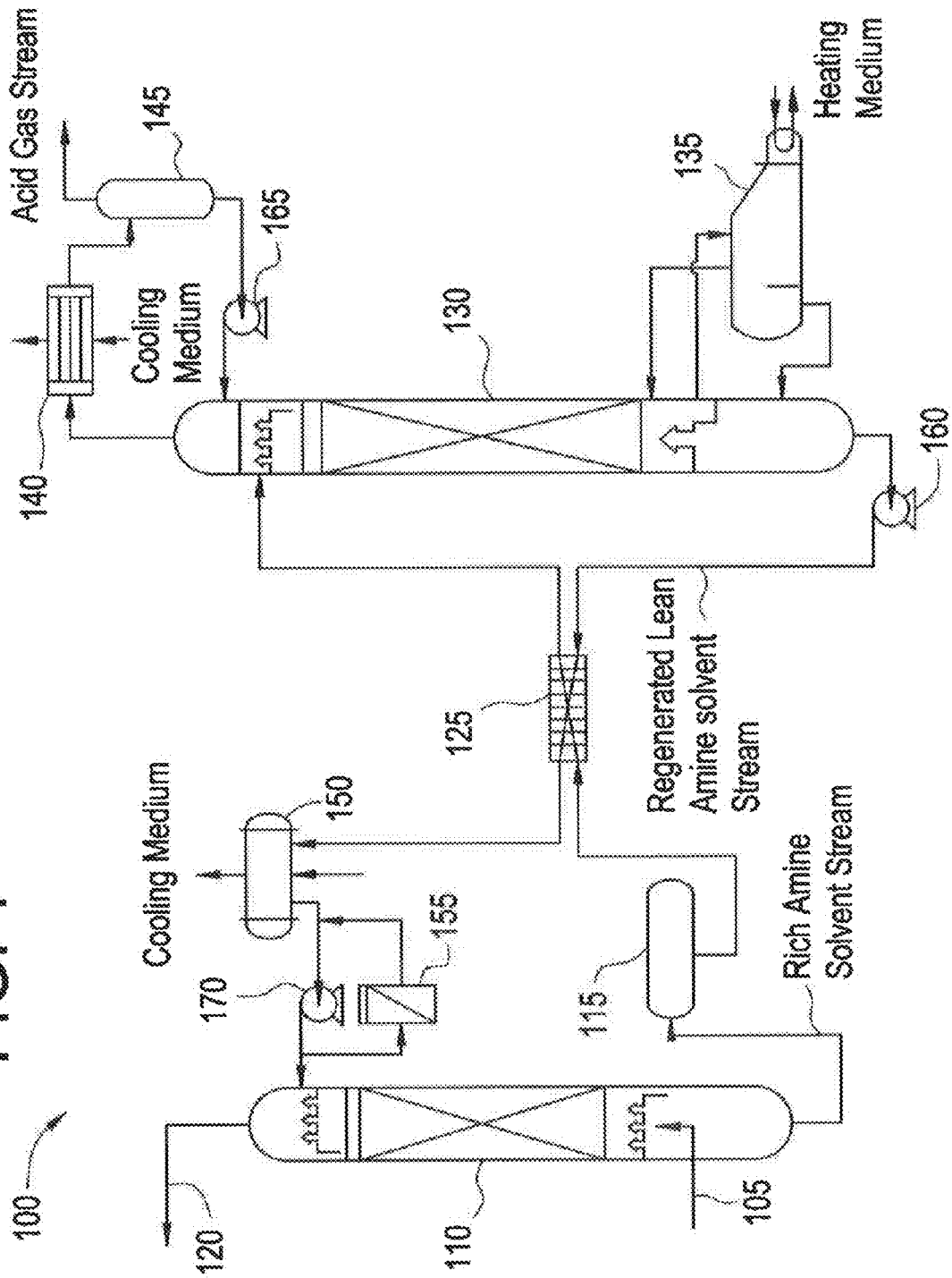
FIG. 1 illustrates a simplified process diagram demonstrating the configuration of the equipment in a typical amine solvent wash system.

Referring to FIG. 1, an exemplary production process (typically found in natural gas processing) where this invention has utility is shown. Production process 100 includes raw gas inlet 105 where gas is contacted counter currently (typically at pressures greater than atmospheric) with a lean solvent solution (i.e., containing very low concentrations of acidic contaminants) in absorber column 110. The rich solvent solution (i.e., containing high concentrations of acidic contaminant(s) absorbed from the feed gas) drains out of absorber column 110 and passes via a pressure reduction valve (not shown) to rich amine flash drum 115 where co-absorbed volatile hydrocarbons and a portion of the absorbed acid gas contaminate is flashed from the solvent and removed into a vapor discharge stream from the drum.

Treated gas outlet 120 contains gas exiting the top of absorber column 110, treated and freed of acid gas contaminant(s). The rich amine solvent exits rich amine flash drum 115 and proceeds through rich/lean amine exchanger 125, where it is heated, and then into the top of regenerator column 130, where the acid gas contaminant(s) is separated from the rich solution at low pressure and high temperature as the solvent flows down the column. The rich solvent is stripped in the column by a countercurrent steam flow produced in amine reboiler 135 at the base of the column. The hot regenerated solvent accumulates at the base of the column and the stripped contaminant(s) gasses exit the top of the column with the stripping steam.

Steam and solvent vapor exiting the top of regenerator column 130 enters acid gas condenser 140. Resulting liquids are collected in reflux drum 145 for circulation back to the top of the regenerator column through reflux circulation pump 165. The regenerated hot lean solvent is pumped from the base of regenerator column 130 via rich/lean exchanger 125 (through lean amine circulation pump 160) and lean amine cooler 150 back into the top of absorber column 110 (through lean amine pressure pump 170), where the cycle is repeated. Filtration of lean solvent at lean amine filter 155 keeps it clear of solids and contaminants including degradation products caused by adverse components of the raw feed gas stream. It should be appreciated that filtration could take place in multiple and various locations in the process.

In one embodiment, the composition of this invention includes at least one substituted cyclic diamine component (as shown in structure (1) above). In a preferred embodiment, the composition of this invention includes substituted piperazine moieties with substitution at the 1 and/or 4 nitrogen positions of the piperazine ring. In other embodiments, the composition includes substituted cyclic diamines having a 4- to 12-membered ring.

Exemplary structures of typical mono- or bi-substituted piperazines of the invention are shown as structure (4) below, where $R_1$ is H, alkyl, aminoalkyl, or structure (5) and R is structure (6) shown below.

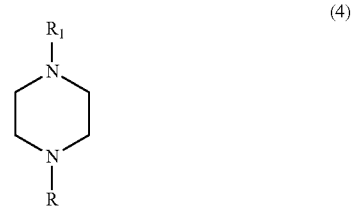

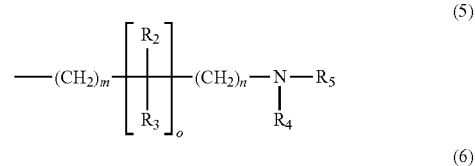

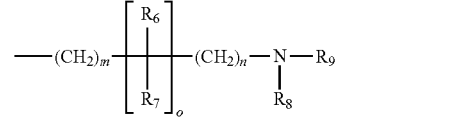

$R_2$, $R_3$, $R_4$, $R_5$, $R_6$, $R_7$, $R_8$, and $R_9$ are independently H, alkyl, or aminoalkyl, and each m, n, and o is independently 0, 1, or 2. In a preferred embodiment, if $R_1$ is H at least one of $R_6$, $R_7$, $R_8$, or $R_9$ is not H, and if $R_1$ is structure (5) at least one of $R_2$, $R_3$, $R_4$, $R_5$, $R_6$, $R_7$, $R_8$, or $R_9$ is not H.

In additional embodiments, the composition of the invention includes a bisubstituted aminopiperazine, which may be symmetric or asymmetric. The substitutions are typically primary linear amines, such as ethylamine or propylamine; secondary linear amines, such as N-methyl-ethylamine; branched amines, such as 2-aminopropyl, 2-aminobutyl, and 3-aminobutyl; and linear alkyl groups. In a preferred embodiment, $R_1$ is a linear amine and R is a branched amine. It should be appreciated that although the symmetrical structures are proficient $CO_2$ absorbents, significant advantages exist in utilizing the asymmetrical variants (i.e., where one of the substituents is a branched amine and the other is a linear amine or linear alkane).

Structure (7) below illustrates a representative structure for the bisubstituted piperazine embodiment of the invention. $R_2$, $R_3$, $R_4$, $R_5$, $R_6$, $R_7$, $R_8$, and $R_9$ are independently H, alkyl, or aminoalkyl. Preferred alkyls include methyl, ethyl, propyl, isopropyl, butyl, and isobutyl. Preferred aminoalkyls include 2-aminopropyl, 2-aminobutyl, aminoethyl, and aminopropyl. In a preferred embodiment, at least one of $R_2$, $R_3$, $R_4$, $R_5$, $R_6$, $R_7$, $R_8$, or $R_9$ is not H. The value of each m, n, and o are independently 0, 1, or 2.

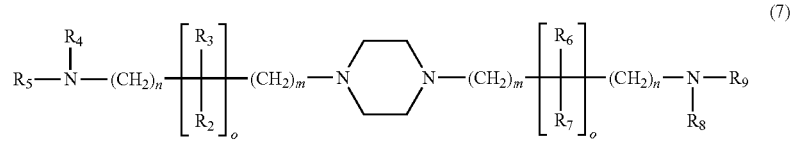

Representative monosubstituted piperazines include 2-aminopropyl-piperazine, and 2-aminobutyl-piperazine. Representative examples of typical bisubstituted piperazines include 1,4-bis-(2-aminopropyl)-piperazine; 1,4-bis-(2-aminobutyl)-piperazine; 1,4-bis-(3-aminobutyl)-piperazone; 1,4-bis-(N-methyl-aminoethyl)-piperazine; 1-(2-aminobutyl)-4-methylpiperazine; 1-(2-aminopropyl)-4-methylpiperazine; and 1-(2-aminopropyl)-4-ethylpiperazine; 1-aminoethyl-4-(2-aminobutyl)-piperazine; 1-aminoethyl-4-(2-aminopropyl)-piperazine; 1-aminopropyl-4-(3-aminobutyl)-piperazine; 1-aminoethyl-4-(N-methyl-aminoethyl)-piperazine; and the like.

In yet another embodiment, the composition of the invention includes a linear or branched polyamine. Structure (8) illustrates a representative structure for this embodiment.

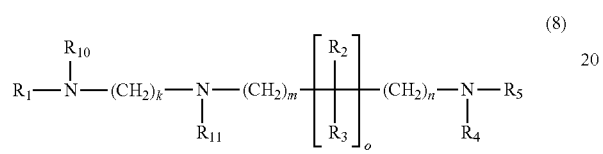
(8)

In an embodiment, $R_1$ is H, alkyl, or structure (9). Preferably, if $R_1$ is H and at least one of $R_2$, $R_3$, $R_4$, $R_5$, $R_{10}$, or $R_{11}$ is not H, and if $R_1$ is structure (9), then at least one of $R_2$, $R_3$, $R_4$, $R_5$, $R_6$, $R_7$, $R_8$, $R_9$, $R_{10}$, or $R_{11}$ is not H.

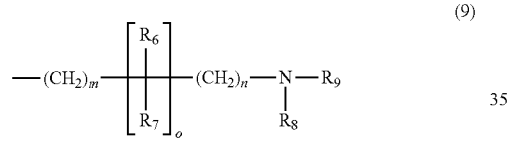
(9)

In another embodiment, $R_2$, $R_3$, $R_4$, $R_5$, $R_6$, $R_7$, $R_8$, $R_9$, $R_{10}$, and $R_{11}$ are independently H, alkyl, or aminoalkyl. Preferred alkyls are methyl, ethyl, propyl, isopropyl, butyl, and isobutyl. Preferred aminoalkyls are 2-aminopropyl, 2-aminobutyl, aminoethyl, and aminopropyl. Each m, n, and o are independently 0, 1, or 2 and k is an integer from 2 to 6. Preferably, k is from 2 to 4.

In one embodiment, the composition of the invention includes an absorbent component of the formula illustrated in structure (I).

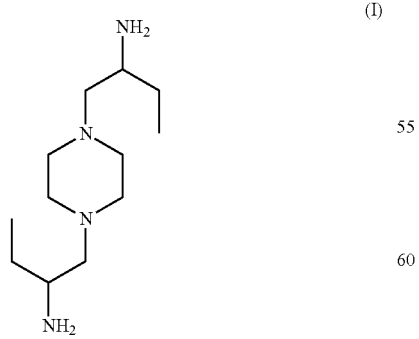
(I)

In another embodiment, the composition of the invention includes an absorbent component of the formula illustrated in structure (II).

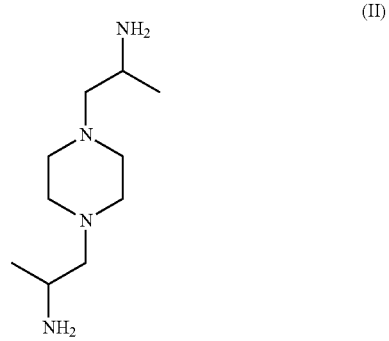
(II)

In an additional embodiment, the composition of the invention includes an absorbent component of the formula illustrated in structure (III).

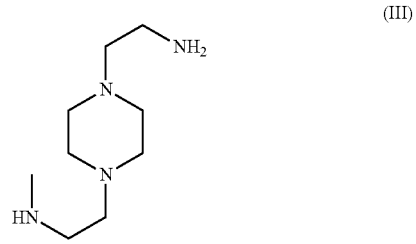
(III)

In yet another embodiment, the composition of the invention includes an absorbent component of the formula illustrated in structure (IV).

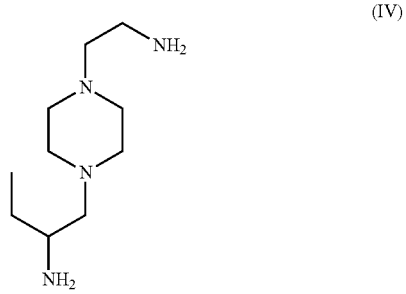
(IV)

In another embodiment, the composition of the invention includes an absorbent component of the formula illustrated in structure (V).

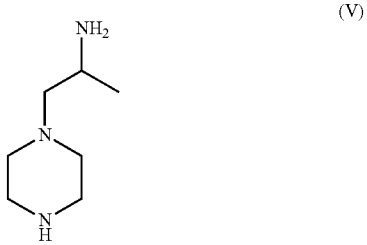
(V)

In another embodiment, the composition of the invention includes an absorbent component of the formula illustrated in structure (VI).

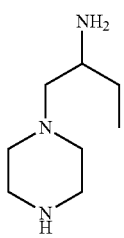

(VI)

In a further embodiment, the composition of the invention includes an absorbent component of the formula illustrated in structure (VII).

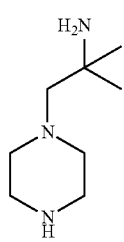

(VII)

In another embodiment, the composition of the invention includes an absorbent component of the formula illustrated in structure (VIII).

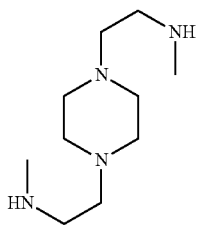

(VIII)

In another embodiment, the composition of the invention includes an absorbent component of the formula illustrated in structure (IX).

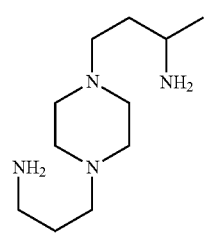

(IX)

In another embodiment, the composition of the invention includes an absorbent component of the formula illustrated in structure (X).

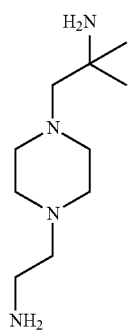

(X)

In another embodiment, the composition of the invention includes an absorbent component of the formula illustrated in structure (XI).

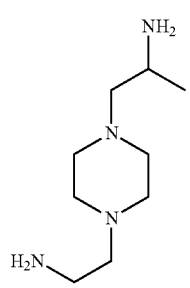

(XI)

In another embodiment, the composition of the invention includes an absorbent component of the formula illustrated in structure (XII).

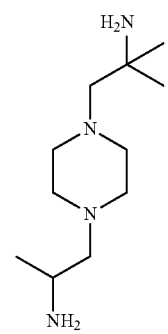

(XII)

In another embodiment, the composition of the invention includes an absorbent component of the formula illustrated in structure (XIII).

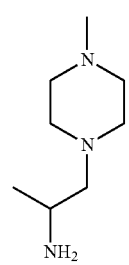

(XIII)

In another embodiment, the composition of the invention includes an absorbent component of the formula illustrated in structure (XIV).

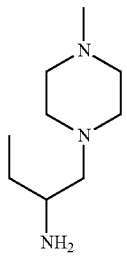
(XIV)

In another embodiment, the composition of the invention includes an absorbent component of the formula illustrated in structure (XV).

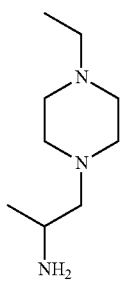
(XV)

In another embodiment, the composition of the invention includes an absorbent component of the formula illustrated in structure (XVI).

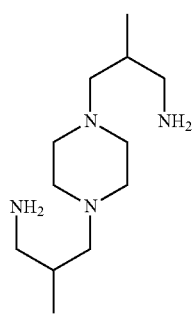
(XVI)

In another embodiment, the composition of the invention includes an absorbent component of the formula illustrated in structure (XVII).

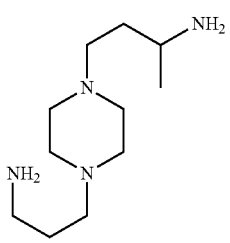
(XVII)

In another embodiment, the composition of the invention includes an absorbent component of the formula illustrated in structure (XVIII).

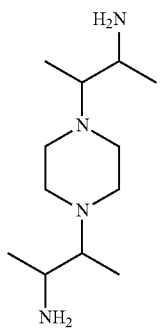
(XVIII)

In another embodiment, the composition of the invention includes an absorbent component of the formula illustrated in structure (XIX).

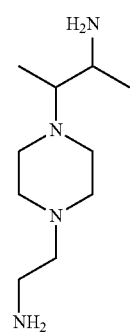
(XIX)

In another embodiment, the composition of the invention includes an absorbent component of the formula illustrated in structure (XX).

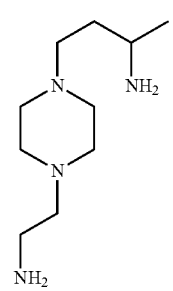
(XX)

In another embodiment, the composition of the invention includes an absorbent component of the formula illustrated in structure (XXI).

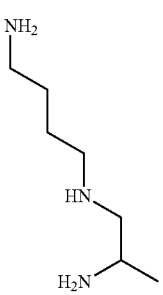
(XXI)

In another embodiment, the composition of the invention includes an absorbent component of the formula illustrated in structure (XXII).

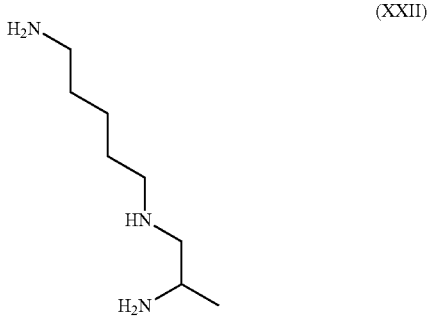

(XXII)

In yet another embodiment, the composition of the invention includes an absorbent component of the formula illustrated in structure (XXIII).

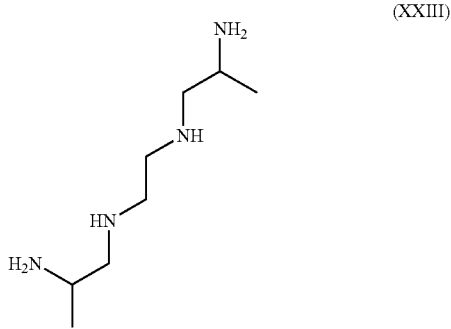

(XXIII)

In yet another embodiment, the composition of the invention includes an absorbent component of the formula illustrated in structure (XXIV).

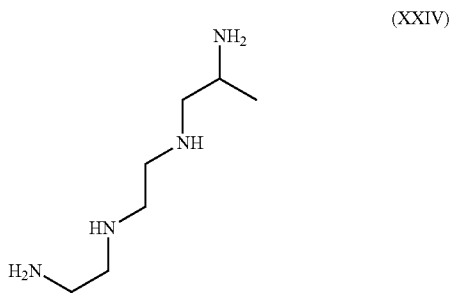

(XXIV)

The composition of the invention may also include derivatives and/or salts of the disclosed structures. Representative derivatives include carbonates, bicarbonates, carbamates, ureas, and amides. Representative salts include all inorganic, mineral, and organic salts.

It is the intent of this invention to use the disclosed structures in a multitude of compositions including single or multiple component solutions in water or as combined with other acid gas solvent components such as tetramethylene sulfone (i.e., Sulfolane), MDEA, DEA, MEA, and the like in water and/or other mutual solvents.

For example, single and multiple component solutions range from about 0.01 to about 100 wt % actives or from about 1 to about 75 wt % actives and include the use of solvents, such as water, alcohols, polyols, other acid gas solvents, and organic solvents. In a preferred embodiment, the composition includes about 10 to about 75 wt % or from about 40 to about 50 wt % actives. Additionally, the composition generally includes an amount of solvent in the range of 0 to 99.09 wt %, depending upon the amount of actives.

The scrubbing liquid used in the composition of the invention may also include, for example, one or more of the following components: aminoethyl-piperazine; 2-aminoethyl-piperazine; 2-aminopropyl-piperazine; 2-aminobutyl-piperazine; 1-acetylpiperazine; 1-formylpiperazine; 1,4-bis-aminoethyl-piperazine; 1,4-bis-aminopropyl-piperazine; 1,4-bisaminobutyl-piperazine; 1,4-bis-(2-aminopropyl)-piperazine; 1,4-bis-(2-aminobutyl)-piperazine; 1,4-bis-(N-methyl-aminoethyl)-piperazine; 1-(2-aminobutyl)-4-methylpiperazine; 1-(2-aminopropyl)-4-methylpiperazine; 1-(2-aminopropyl)-4-ethylpiperazine; 1-aminoethyl-4-(2-aminobutyl)-piperazine; 1-aminoethyl-4-(2-aminopropyl)-piperazine; 1-aminoethyl-4-(N-methyl-aminoethyl)-piperazine; 2-morpholinoethanamine; 2-aminopropyl-morpholine; 2-(1H-imidazol-1-yl)ethanamine; 2-aminopropyl-piperidine; 2-aminopropyl-pyrrolidine; N1-(2-aminopropyl)butane-1,4-diamine; N1-(3-aminopropyl) propane-1,2-diamine; water; sulfolane, N-methylpyrrolidone; N-alkylated pyrrolidones, piperidones and morpholines corresponding to the foregoing; methanol; mixtures of dialkyl ethers of polyethylene glycols; $C_1$ to $C_4$ dialkylether monoethylene glycols; $C_1$ to $C_4$ monoether monoethylene glycols; $C_1$ to $C_4$ dialkylether poly ethylene glycols; $C_1$ to $C_4$ monoether polyethylene ethylene glycols; $C_1$ to $C_4$; ethylene glycol; diethylene glycol; triethylene glycol; N,N-dimethyl formamide; N-acetyl morpholine; N-formyl morpholine; N,N-dimethyl imidazolidin-2-one; N-methyl imidazole; and the like.

In another embodiment, the composition of the invention may also include other components. Representative other components include blends of amines, activators, antifoaming agents, co-absorbents, corrosion inhibitors, solvents, coloring agents, the like, and combinations thereof. Representative examples include alkanolamines; cyclotetramethylene sulfone and its derivatives; aliphatic acid amines such as acetyl morpholine or N-formyl morpholine; alkali metal compounds which provide alkaline hydrolysis products, such as alkali metal hydrolysis and hydrocarbonates; aliphatic and cycloaliphatic mono- and diamines, such as triethylene diamine, dicyclohexyl amine, N-ethyl-cyclohexylamine, and N,N-diemthylcyclohexylamine; the like; and combinations thereof.

In another embodiment, coabsorbents include one or more components selected from calcium oxide, calcium lignosulfonate, calcium silicate hydrates, calcium hydroxide, calcium carbonate, calcium bicarbonate, sodium carbonate, sodium bicarbonate, trona, sodium sesquicarbonate, soda ash, nacholite, sodium aluminate, metal oxides, and the like.

Activators and coabsorbents are preferably present in the composition of the invention from about 0.01 to about 90 wt %, more preferably from about 1 to about 50 wt %, and most preferably from about 1 to about 25 wt % (wt % based on the weight of total actives).

In a further embodiment, the invention is a process for reducing acidic contaminants in an industrial fluid stream. The fluid stream is contacted with the disclosed composition to form a washed fluid stream and a rich acid gas scrubbing liquid. Typically, the composition is contacted with the gas stream at a temperature ranging from about 0 to about 200° C. In certain cases, this temperature range may be from about 0 to about 100° C. or from about 20 to about 65° C. Industrial processes generally run at a pressure ranging from about 0 to about 200 atm, from about 0 to about 100 atm, from about 0 to about 70 atm, from about 0 to about 50 atm, from about 0 to about 25 atm, from about 0 to about 10 atm, or from about 1 to about 5 atm during the time when the composition is contacted with the fluid stream. U.S. Pat. No. 4,556, "Bis Tertiary Amino Alkyl Derivatives as Solvents for Acid Gas Removal from Gas Streams" discloses pressure ranges from 4 to 70 atm. Canadian patent application no. 2,651,888, "Carbon Dioxide Absorbent Requiring Less Regeneration Energy" discloses pressures from 1 to 120 atm. It should be appreciated that this invention is operable in any of these or other pressure ranges encountered in the relevant art.

The rich acid gas scrubbing liquid is further processed through a regeneration system where at least a portion of the composition including at least a portion of the absorbent compound(s) contacted with the fluid stream are regenerated. The regeneration step normally takes place at a higher temperature than absorption (depending on the particular industrial process), usually at a temperature ranging from about 0 to about 500° C., from about 20 to about 250° C., or from about 50 to about 150° C. The pressure range for the regeneration step is normally from about 0 to about 10 atm or from about 1 to about 5 atm. In certain cases, the regeneration step may be carried out via a steam-assisted reboiler. Regeneration may also be carried out via a fractional regeneration process (e.g., WO 2007/077323, "Method for Deacidifying a Gas with a Fractionally-Regenerated Absorbent Solution with Control of the Water Content of the Solution").

The foregoing may be better understood by reference to the following examples, which are intended for illustrative purposes and are not intended to limit the scope of the invention.

Example 1

The testing in this Example was used as a means of screening potential acidic contaminant scavengers and also to confirm the performance of existing commercially available scavengers. The test was designed to determine the maximum capacity of an amine solvent in absorbing acidic gases. Different amine solvents were compared. The amine solvents were saturated with acidic gases at a constant pressure and temperature until no more gas was able to be absorbed. The difference between the rich and lean loadings was used to determine the working capacity. The test was designed to regenerate the solvent by boiling to remove the acidic gases so that the lean loading of $CO_2$ in an amine solvent could be determined.

Solvent performance was characterized by liquid loading at equilibrium with defined composition gas mixtures at simulated amine contactor and regenerator conditions relative to industry benchmarks.

Figure 2:
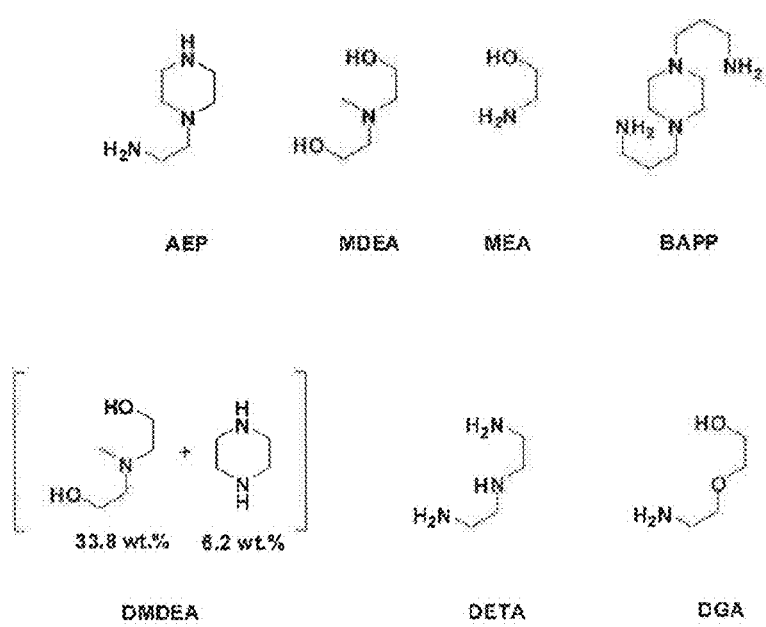
FIG. 2 shows the common commercially available $CO_2$ absorbents used for the comparative testing discussed in Example 1.

To highlight the advantages of the disclosed novel amines, several specific samples were benchmarked against common commercial $CO_2$ absorbents (such as methyldiethanolamine (MDEA), 33.8/6.2 methyldiethanolamine/piperazine (DMDEA), diglycolamine (DGA), monoethanolamine (MEA), aminoethyl-piperazine (AEP), and bisaminopropylpiperazine (BAPP), illustrated in FIG. 2) using a laboratory-scale fixed bed absorption cell and a batch reboiler. The "Sorbent" numbers indicated in Table 1 correspond to the structure numbers above. The equilibrium saturation test to determine the rich loading (weight % CO2 absorbed by fresh sorbent) was run by exposing an aqueous solution of the absorbent at 40° C. to 30 psi of $CO_2$ until saturation was reached. The lean loading (weight % $CO_2$ remaining associated with the absorbent after regeneration) was determined by refluxing the aqueous solution of the absorbents for two hours at atmospheric pressure. The working capacity is defined as the rich loading minus the lean loading. It is the working capacity that most accurately reflects the capacity of the chemical to absorb $CO_2$ under process conditions. The results of this evaluation are reported in Table 1.

To determine rich loading, the equipment consisted of a high pressure gas panel that was capable of receiving supplies of 100% $CO_2$, $CO_2/N_2$ mixtures and $CO_2/H_2S/N_2$ mixtures. The chosen gas was fed via a mass flow controller (Sierra series 100 mass flow controller, available from Sierra Instruments, Inc. in Monterey, Calif.) to the reaction vessel. A gas totalizer (a Sierra Compod) attached to the mass flow controller measured the volume of gas used.

Once the appropriate gas cylinder valve and regulators were opened, the recirculating bath was set to a temperature of 40° C. A 200 ml glass reaction vessel was attached to the head of a Buchi Picoclave. The inlet and outlet valves to the reaction vessel were closed and the inlet pressure regulator was set to 30 psi. The gas mixture was set to 100% $CO_2$ and the flow rate was set to 0.5 liters/min. After allowing the gas pressure to build to 30 psi at the reactor inlet, the amine solution was prepared at the concentration indicated in Table 1 and, after being brought to the same temperature as the reaction vessel, was added to the reaction vessel and stirred at 1,000 rpm.

The inlet valve was opened and the reactor pressure was allowed to equilibrate to 30 psi. When the pressure in the reactor reached 30 psi, the inlet valve was closed the inlet valve and the gas flow was shut off. The volume in the reactor vessel was recorded. Gas flow was resumed after 5 minutes and continued until the pressure equalized to 30 psi. This procedure was repeated until no additional $CO_2$ was absorbed as measured by the final volume. The wt % rich loading of the amine was calculated from the final volume of $CO_2$ absorbed.

To determine lean loading, the amine composition to be regenerated was poured into a 250 ml 3-neck flask equipped with mechanical stirring and a chilled condenser (8° C.). The amine solution was slowly heated to 150° C. to help avoid a sudden release of gas which would have caused the solution to foam. The solution was refluxed for 2 hours and then cooled to room temperature. The lean loading of the amine was determined via a standard barium chloride back titration.

To determine depth of removal, a mass flow controller (Sierra series 100 mass flow controller) was used to control the flow of gas through the reactor vessel. The chosen gas was fed via the mass flow controller to the saturation vessel (which contained deionized water) and then into the reaction vessel. From the reaction vessel, the gas was fed via a backpressure regulator through a Dreschel bottle containing ethylene glycol and a drying tube containing silica gel to the $CO_2$ analyzer. The $CO_2$ analyzer (Signal 7000FM $CO_2$ analyzer) recorded the concentration of $CO_2$ flowing through it. The recirculating bath was set to the required temperature of 40° C. The 200 ml glass reaction vessel was fitted to the head of a Buchi Picoclave. A Dreschel bottle containing ethylene glycol and a drying tube containing silica gel was connected to the gas line prior to the $CO_2$ analyzer, and the backpressure regulator was set to 90 psi. The gas mixture (25% $CO_2$/75% $N_2$) and the flow rate (0.45 liters/min) were then set and allowed to stabilize for 30 minutes. The amine solution was prepared at the concentrations indicated in Table 1 and heated as above. The amine was then added to the reaction vessel and the stirrer was set to 1,000 rpm. The downstream regulator was closed and the data recording began. The gas flow was allowed to continue until equilibrium was reached ~3 hrs. At the end of the run, the gas flow was stopped, the inlet valve to the reaction vessel was closed, and the data recording was stopped.

TABLE 1

NPX Amines vs. Common Absorbents

| Sorbent | MW | Wt. % (Aq) | Rich Loading | Rich Mole Ratio | Lean Loading | Lean Mole Ratio | Working Capacity | Working Mole Ratio | Depth of Removal |
|---|---|---|---|---|---|---|---|---|---|
| XXII | 145.25 | 43.5% | 17.64% | 1.63 | 1.97% | 0.15 | 15.67% | 1.41 | 0.00% |
| XXI | 131.21 | 39.3% | 17.54% | 1.61 | 2.21% | 0.17 | 15.33% | 1.37 | NA |
| XIII | 157.26 | 40.0% | 13.58% | 1.40 | 0.09% | 0.01 | 13.49% | 1.39 | 0.41% |
| XI | 186.3 | 40.0% | 13.28% | 1.62 | 0.19% | 0.02 | 13.09% | 1.59 | 0.10% |
| X | 200.32 | 40.0% | 11.31% | 1.45 | 0.22% | 0.03 | 11.09% | 1.42 | 0.15% |
| VI | 157.26 | 40.0% | 12.74% | 1.30 | 0.04% | 0.00 | 12.70% | 1.30 | 0.18% |
| IV | 200.32 | 40.0% | 11.78% | 1.52 | 0.20% | 0.02 | 11.58% | 1.49 | 0.24% |
| II | 200.32 | 40.0% | 13.27% | 1.74 | 0.06% | 0.01 | 13.21% | 1.73 | NA |
| I | 228.38 | 40.0% | 11.79% | 1.73 | 0.00% | 0.00 | 11.79% | 1.73 | 0.35% |
| MDEA | 119.16 | 40.0% | 10.88% | 0.83 | 0.00% | 0.00 | 10.88% | 0.83 | 1.63% |
| DMDEA | 114.41 | 40.0% | 11.27% | 0.83 | 0.03% | 0.00 | 11.24% | 0.82 | 0.35% |
| DGA | 105.14 | 40.0% | 9.43% | 0.62 | 0.13% | 0.01 | 9.30% | 0.61 | 0.11% |
| MEA | 61.08 | 35.0% | 13.50% | 0.62 | 1.41% | 0.06 | 12.09% | 0.55 | 0.00% |

The tested amines on average absorbed about 1.5 moles of $CO_2$ per mole of absorbent compared to less than 1 mole of $CO_2$ per mole of the common absorbents. Although not all the tested amines outperformed the common absorbents, Sorbents II, VI, XI, XIII, XXI, and XXII showed a significant increase in working capacity (5 to 30% increase based on MEA). These amines, with the exception of Sorbents XXI and XXII, also have a significantly lower lean loading than MEA.

The boiling points of the disclosed amines range from about 200 to about 280° C. at 1atm (compared to MEA at 170° C. and 1atm). Such higher boiling points help significantly reduce the losses and potential environmental releases currently associated with the volatility of MEA and also help to prevent $CO_2$ contamination during solvent regeneration. Initial laboratory stability testing has indicated that unlike MEA, which is known to degrade rapidly under process condition, the disclosed amines are highly robust at simulated process conditions showing no signs of degradation.

To further highlight the utility of the tested amines for carbon capture, a 25% $CO_2$ gas stream at 90 psi was passed through the absorbents at 40° C. until they reached saturation and the depth of removal was recorded. Importantly, the depth of removal for many of the tested amines approached 0%, an indication that they are highly efficient at $CO_2$ capture as shown in Table 1.

Example 2

Although a reduction in the lean loading of branched compounds over linear compounds would have been expected, the select group of molecules tested showed a unique increase in the working capacity of the branched targets (Table 2). The "Sorbent" numbers indicated in Table 2 correspond to the structure numbers above. This unusual reactivity is particularly evident when comparing the linear BAPP to the branched Sorbent II. The two molecules are identical in molecular weight and were tested under identical conditions; however, Sorbent II shows a 9.5% increase in working capacity. This unexpected and surprising increase in capacity is thought to occur via a change in the mechanism by which the amine reacts with $CO_2$. It has been proposed that the linear amine favors direct reaction with the $CO_2$ to form the carbamate, and the branched amine favors (similar to tertiary amines) indirect reaction with the $CO_2$ to form a bicarbonate salt. Thus, the reaction between $CO_2$ and the branched amines are of greater efficiency.

TABLE 2

Branched vs. Linear

| Sorbent | Branched/ Linear | MW | Wt. % (Aq) | Working Mole Ratio | Lean Mole Ratio | % Increase |
|---|---|---|---|---|---|---|
| XIII | Branched | 157.26 | 40.00% | 1.39 | 0.01 | 17.80% |
| VI | Branched | 157.26 | 40.00% | 1.30 | 0.00 | 10.17% |
| AEP | Linear | 129.20 | 40.00% | 1.18 | 0.05 | 0.00% |
| II | Branched | 200.32 | 40.00% | 1.73 | 0.01 | 9.49% |
| I | Branched | 228.38 | 40.00% | 1.73 | 0.00 | 9.49% |
| BAPP | Linear | 200.32 | 40.00% | 1.58 | 0.14 | 0.00% |
| XXII | Branched | 145.25 | 43.50% | 1.41 | 0.15 | 12.80% |
| XXI | Branched | 131.21 | 39.30% | 1.37 | 0.17 | 9.60% |
| DETA | Linear | 103.17 | 30.90% | 1.25 | 0.19 | 0.00% |

Example 3

This Example compared the absorption data of AEP and Sorbents VI and XIII. The testing revealed that alkyl substitution of one of the piperazine nitrogens with small alkyl groups (such as methyl and ethyl) afforded an unexpected increase in the capacity of the sorbent (Table 3). The "Sorbent" numbers indicated in Table 3 correspond to the structure numbers above. Sorbents VI and XIII showed an increase in capacity over the linear AEP, but unlike Sorbents I and II, which had an equal increase regardless of the length of the alkyl branch (ethyl vs. methyl), Sorbent XIII showed a significant increase in capacity over Structure VI.

TABLE 3

Alkyl Substitution of Piperazine

| Sorbent | Branched/ Linear | MW | Wt. % (Aq) | Working Mole Ratio | Lean Mole Ratio | % Increase |
|---|---|---|---|---|---|---|
| XIII | Branched | 157.26 | 40.00% | 1.39 | 0.01 | 17.80% |
| VI | Branched | 157.26 | 40.00% | 1.30 | 0.00 | 10.17% |
| AEP | Linear | 129.20 | 40.00% | 1.18 | 0.05 | 0.00% |

Example 4

This Example illustrates that absorbents with asymmetrical substitution (e.g., a branched amine and a linear amine) demonstrated reduced depth of removal with little to no penalty in terms of working capacity and lean loading (Table 4). The "Sorbent" numbers indicated in Table 4 correspond to the structure numbers above.

TABLE 4

Asymmetrical Substitution

| Sorbent | MW | Wt. % (Aq) | Working Mole Ratio | Lean Mole Ratio | Depth of Removal |
|---------|--------|------------|--------------------|-----------------|------------------|
| XI      | 186.3  | 40.0%      | 1.59               | 0.02            | 0.10%            |
| X       | 200.32 | 40.0%      | 1.42               | 0.03            | 0.15%            |
| IV      | 200.32 | 40.0%      | 1.49               | 0.02            | 0.24%            |
| I       | 228.38 | 40.0%      | 1.73               | 0.00            | 0.35%            |
| BAPP    | 200.32 | 40.0%      | 1.58               | 0.14            | 0.16%            |

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein and parent or continuation patents or patent applications, are hereby incorporated by reference in their entirety. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

The claimed invention is:

1. A process for reducing acidic contaminants in an industrial fluid stream, the process comprising: (I) contacting the fluid stream with a scrubbing liquid composition for absorbing acidic contaminants from fluids in an industrial process, the composition comprising:
   (a) at least one absorbent component having a general formula, including carbonates, bicarbonates, carbamates, ureas, and amides thereof and salts thereof:

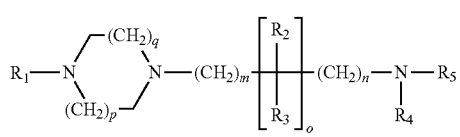

wherein o is 1 or 2,
   (i) $R_1$ is selected from the group consisting of: H, alkyl, aminoalkyl, and the following structure (A),

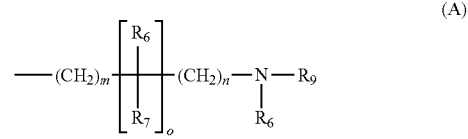

wherein o is 0, 1 or 2,
   (ii) $R_2$, $R_3$, $R_4$, $R_5$, $R_6$, $R_7$, $R_8$, and $R_9$ are independently H, alkyl, or aminoalkyl; wherein at least one of $R_2$ and $R_3$ is not H,
   (iii) each m, and n, is independently 0, 1, or 2,
   (iv) p and q are independently 0, 1, 2, 3, or 4; and
(b) a solvent;
(II) forming a washed fluid stream and a rich acid gas scrubbing liquid; and
(III) regenerating at least a portion of the composition including at least a portion of the absorbent compound(s) from the rich acid gas scrubbing liquid.

2. The process of claim 1, wherein the alkyl for R1 to R9 is independently selected from the group consisting of: methyl, ethyl, propyl, isopropyl, butyl, and isobutyl.

3. The process of claim 1, wherein the aminoalkyl for R1 to R9 is selected from the group consisting of: 2-aminopropyl, 2-aminobutyl, aminoethyl, and aminopropyl.

4. The process of claim 1, wherein said absorbent component is selected from the group consisting of: (I), (II), (IV), (V), (VI), and combinations thereof:

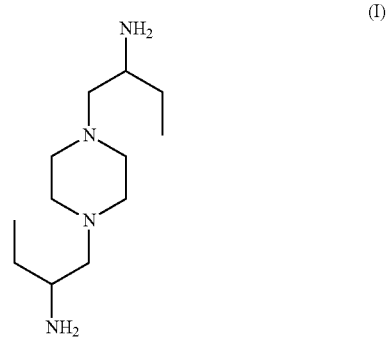

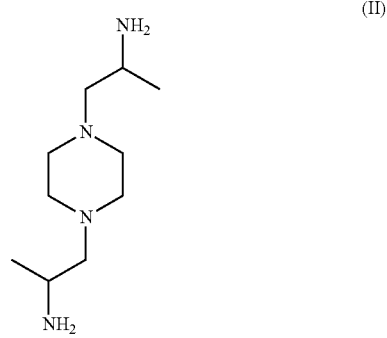

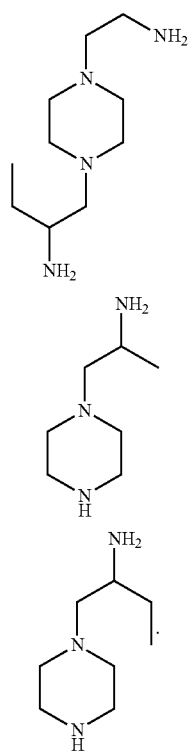
5. The process of claim 1, wherein said absorbent component is selected from the group consisting of: (VII), (IX), (X), (XI), (XII), and combinations thereof:
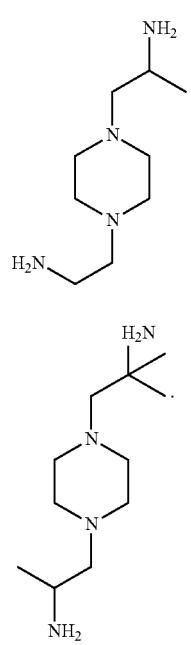
6. The process of claim 1, wherein said absorbent component is selected from the group consisting of: (XIII), (XIV), (XV), (XVI), (XVII), (XVIII), (XIX), (XX), and combinations thereof:
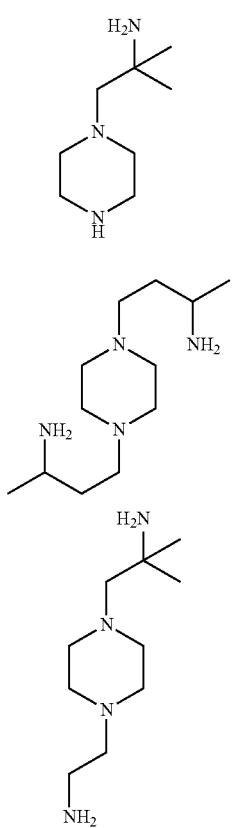

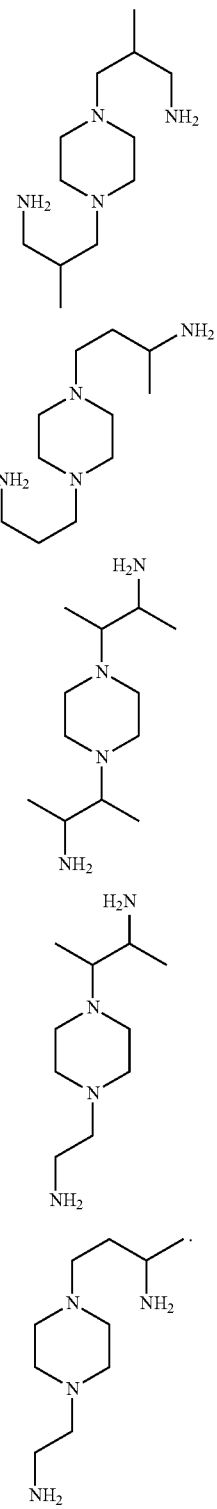

(XVI)

(XVII)

(XVIII)

(XIX)

(XX)

7. The process of claim 1, wherein the acidic contaminant is selected from the group consisting of $CO_2$, $H_2S$, RSH, $CS_2$, COS, $SO_2$, and combinations thereof.

8. The process of claim 1, Wherein said absorbent compound is present in an amount ranging from about 0.01 to about 100 wt%.

9. The process of claim 1, further comprising one or more components selected from the group consisting of: amines, activators, antifoaming agents, co-absorbents, corrosion inhibitors, coloring agents, and combinations thereof.

10. The process of claim 1, wherein the solvent is selected from the group consisting of: water, alcohols, polyols, other acid gas solvents, organic solvents, and combinations thereof.

11. The process of claim 1, wherein step (I) of the process is performed in a temperature range from about 0 to about 200° C.

12. The process of claim 1, wherein step (I) of the process is performed at a pressure range from about 0 to about 200 atm.

13. The process of claim 1, wherein step (III) is carried out in a temperature range from about 0 to about 500° C.

14. The process of claim 1, wherein step (III) is carried out at a pressure range from about 0 to about 10 atm.

15. The process of claim 1, wherein step (III) is carried out via a steam-assisted reboiler.

16. The process of claim 1, wherein step (III) is carried out via fractional regeneration.

17. The process of claim 1, wherein the absorbent component is selected from the following group: 2-aminopropyl-piperazine; 2-aminobutyl-piperazine; 1,4-bis-(2-aminopropyl)-piperazine; 1,4-bis-(2-aminobutyl)-piperazine; 1-(2-aminobutyl)-4-methylpiperazine; 1-(2-aminopropyl)-4-methylpiperazine ; 1-(2-aminopropyl)-4- ethylpiperazine; 1-aminoethyl-4-(2-aminobutyl) -piperazine; 1-aminoethyl -4-(2-aminopropyl)-piperazine; and combinations thereof.

18. The process of claim 1, further comprising an additional absorbent component selected from the following group: 1-formylpiperazine; 2-morpholinoethanamine; 2-aminopropyl -morpholine; 2-(1H-imidazol-1-yl)ethanamine; 2-aminopropyl-piperidine; 2-aminopropyl -pyrolidine; N1-(2- aminopropyl)butane- 1,4-diamine; N1-(3-aminopropyl)propane-1,2-diamine; and combinations thereof.

19. The process of claim 1, wherein the solvent is selected from the following group; water; sulfolane, N-methylpyrrolidone; N-alkylated pyrrolidones, piperidones and morpholines corresponding to the foregoing; methanol; mixtures of dialkyl ethers of polyethylene glycols; $C_1$ to $C_4$ dialkylether monoethylene glycols; $C_1$ to $C_4$ monoether monoethylene glycols; $C_1$ to $C_4$ dialkylether poly ethylene glycols; $C_1$ to $C_4$ monoether polyethylene ethylene glycols; $C_1$ to $C_4$; ethylene glycol; diethylene glycol; triethylene glycol; N,N-dimethyl formamide; N-acetyl morpholine; N-formyl morpholine; N,N-dimethyl imidazolidin-2-one; N-methyl imidazole; and combinations thereof.

20. A process for reducing acidic contaminants in an industrial fluid stream, the process comprising: (I) contacting the fluid stream with a scrubbing liquid composition for absorbing acidic contaminants from fluids in an industrial process, the composition comprising:
(a) at least one absorbent component selected from the following, including carbonates, bicarbonates, carbamates, ureas, and amides thereof and salts thereof:

(II)

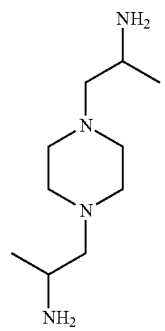

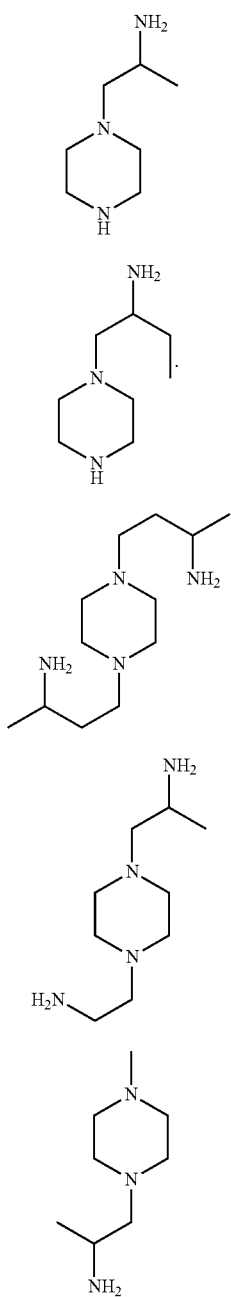
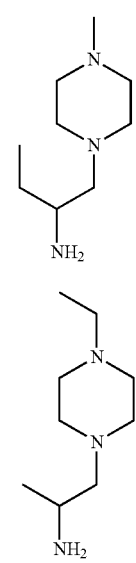
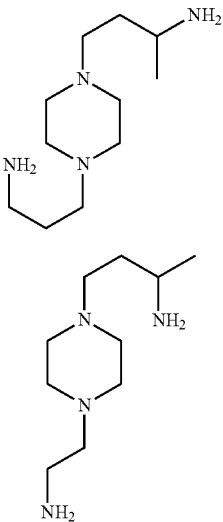
(b) a solvent;
(II) forming a washed fluid stream and a rich acid gas scrubbing liquid; and
(III) regenerating at least a portion of the composition including at least a portion of the absorbent compound(s) from the rich acid gas scrubbing liquid.
* * * * *

UNITED STATES PATENT AND TRADEMARK OFFICE
CERTIFICATE OF CORRECTION

| | | |
|---|---|---|
| PATENT NO. | : 8,551,435 B2 | Page 1 of 1 |
| APPLICATION NO. | : 13/397131 | |
| DATED | : October 8, 2013 | |
| INVENTOR(S) | : Blair et al. | |

It is certified that error appears in the above-identified patent and that said Letters Patent is hereby corrected as shown below:

In the Claims,
Claim 1 item (i) at column 20, line number 12 remove "$R_6$" and replace with "$R_8$".

Signed and Sealed this
Twenty-fourth Day of November, 2015

Michelle K. Lee
*Director of the United States Patent and Trademark Office*